(12) United States Patent
Ziembinski

(10) Patent No.: US 8,252,094 B2
(45) Date of Patent: Aug. 28, 2012

(54) GAS EXCHANGE MEMBRANE IN PARTICULAR FOR USE IN AN ARTIFICIAL LUNG AND METHOD FOR THE PRODUCTION OF A GAS EXCHANGE MEMBRANE OF THIS TYPE

(75) Inventor: Ralf Ziembinski, Brunnenthal (DE)

(73) Assignee: Raumedic AG, Muenchberg (DE)

( * ) Notice: Subject to any disclaimer, the term of this patent is extended or adjusted under 35 U.S.C. 154(b) by 487 days.

(21) Appl. No.: 12/522,815

(22) PCT Filed: Jan. 8, 2008

(86) PCT No.: PCT/EP2008/000057
§ 371 (c)(1),
(2), (4) Date: Jul. 10, 2009

(87) PCT Pub. No.: WO2008/083943
PCT Pub. Date: Jul. 17, 2008

(65) Prior Publication Data
US 2010/0050875 A1    Mar. 4, 2010

(30) Foreign Application Priority Data
Jan. 11, 2007 (DE) .......................... 10 2007 001 665

(51) Int. Cl.
*B01D 53/22* (2006.01)
*B01D 67/00* (2006.01)
*B01D 71/70* (2006.01)
*A61M 1/16* (2006.01)
*B29C 44/34* (2006.01)

(52) U.S. Cl. ................. 96/8; 96/6; 96/10; 96/12; 95/46; 95/51; 95/54; 264/45.9; 264/54; 604/4.01; 604/6.14

(58) Field of Classification Search ................... 96/4, 6, 96/8, 10, 12; 95/45, 46, 51, 54; 55/DIG. 5; 264/45.9, 54; 604/4.01, 6.14
See application file for complete search history.

(56) References Cited

U.S. PATENT DOCUMENTS 4,666,668 A * 5/1987 Lidorenko et al. ................. 96/6
5,853,633 A * 12/1998 Kono et al. ..................... 264/54
5,964,725 A * 10/1999 Sato et al. .................... 604/4.01

FOREIGN PATENT DOCUMENTS

| DE | 38 77 751 T2 | 5/1993 |
|---|---|---|
| DE | 42 38 884 A1 | 5/1994 |
| DE | 38 50 344 T2 | 11/1994 |
| DE | 100 12 308 A1 | 9/2001 |
| DE | 100 34 098 A1 | 1/2002 |
| DE | 697 19 835 T2 | 12/2003 |
| DE | 600 03 112 T2 | 5/2004 |
| DE | 100 17 690 A1 | 10/2005 |
| EP | 0 754 488 A1 | 1/1997 |

(Continued)

*Primary Examiner* — Jason M Greene
(74) *Attorney, Agent, or Firm* — Browdy and Neimark, PLLC

(57) ABSTRACT

A gas exchange membrane is for use in an artificial lung. The membrane consists of a foamed, closed-cell material, in particular of silicone rubber. The membrane is produced by extruding a basic material which contains a foaming agent. The extrudate is then foamed. The result is a gas exchange membrane which has an increased gas exchange performance compared to known material due to the high permeability of the surface.

15 Claims, 1 Drawing Sheet

FOREIGN PATENT DOCUMENTS

| | | |
|---|---|---|
| EP | 0 803 259 A1 | 10/1997 |
| EP | 0 765 683 B1 | 7/1998 |
| JP | 2004 050042 A | 2/2004 |
| WO | 99/38604 A1 | 8/1999 |
| WO | 00/26006 A1 | 5/2000 |
| WO | 02/04554 A1 | 1/2002 |

\* cited by examiner

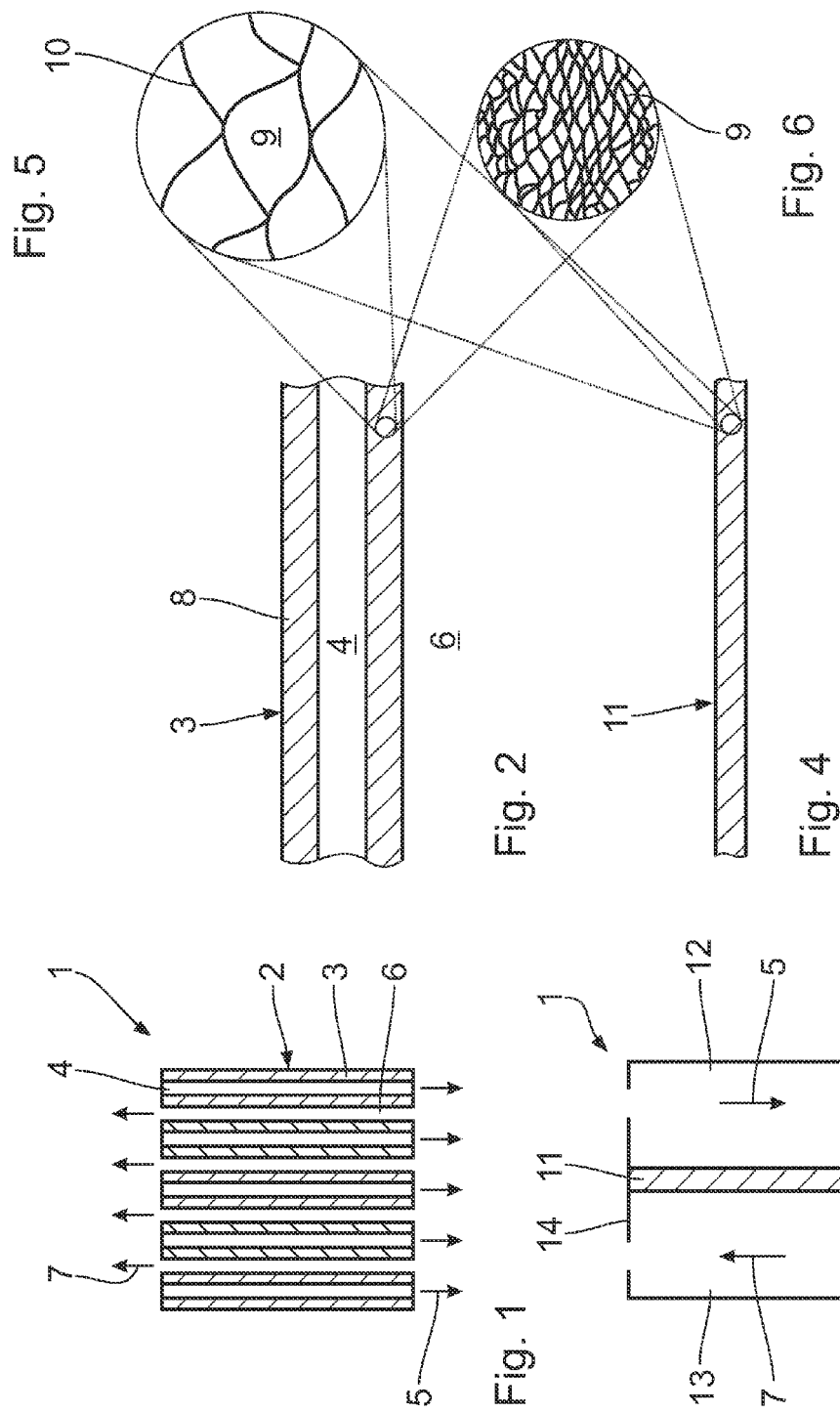

GAS EXCHANGE MEMBRANE IN PARTICULAR FOR USE IN AN ARTIFICIAL LUNG AND METHOD FOR THE PRODUCTION OF A GAS EXCHANGE MEMBRANE OF THIS TYPE

BACKGROUND

1. Field

The invention relates to a gas exchange membrane for a medical application, in particular for use in an artificial lung. The invention further relates to a method for the production of a gas exchange membrane of this type.

2. Background

Gas exchange media of this type are for instance disclosed in EP 0 765 683 B1, in EP 0 803 259 A1, in DE 42 38 884 A1, in DE 600 03 112 T2 and in DE 100 34 098 A1. The gas exchange membrane is applied in an oxygenator in order to transport oxygen to blood or blood plasma and in order to remove carbon dioxide, which is produced by metabolic activity, from the blood or blood plasma. The gas exchange membrane is in particular known in the form of a hollow fiber membrane. In conventional oxygenators, the hollow fibers are for instance made of polypropylene (PP) or of polymethylpentene (PMP). Both materials are polymers of the polyolefins and have poor blood compatibility. When these materials are used, an activation of the blood coagulation system, primarily of the thrombocytes, can be observed. Moreover, defects or leaks in the known hollow fibers may cause blood or blood plasma to escape from the blood circulation of the oxygenator, with the undesirable result that blood or blood plasma reaches the non-sterile side of the gas exchange membrane. Due to the limited gas exchange performance of conventional hollow fiber membranes, conventional oxygenators are quite voluminous. The disadvantage of the large volume of conventional oxygenators is that a considerable amount of blood or blood plasma needs to be provided for the exchange of gas. Gas exchange membranes are also used in other medical applications, for instance as pads for the treatment of burns.

EP 0 754 488 describes gas separation membranes, for instance for medical applications.

JP 2004/050042 A describes a membrane module of a silicone foam for gas separation.

DE 100 12 308 A1 describes hollow fiber membranes which are both applicable for gas exchange and for separation processes. The hollow fibers are spun. The disclosure suggests a method of producing cells by adding foaming agents.

WO 99/38604 A1 discusses several disclosures which have dealt with the fabrication of open-cell and closed-cell membranes.

WO 02/04554 A1 describes a gas- or liquid-permeable bicontinuous foam structure.

WO 00/26006 A1 describes a method of producing microcellular foams for the production of molded articles.

SUMMARY

It is therefore an object of the present invention to improve a gas exchange membrane of the type described at the outset in such a way that the gas exchange performance thereof is increased.

This object is achieved by a gas exchange membrane for a medical application, in particular for use in an artificial lung, comprising an arrangement of foamed, closed-cell material, in particular of foamed, closed-cell silicone rubber.

The closed-cell foamed material according to the invention ensures a good separation of the gas side from the blood side of the gas exchange membrane, thus preventing an unwanted escape of blood or blood plasma to the gas side. Moreover, foamed material can be produced into gas exchange media with a gas exchange performance which clearly exceeds that of conventional hollow fibers. The increased gas exchange performance is due to the considerably higher gas permeability of the material used for the gas exchange membrane according to the invention. This allows compact oxygenators to be developed which only require a smaller volume of blood compared to the prior art. This reduces the amount of blood required for an operation. Typical gas exchange surface areas are between 1 and 2 $m^2$. It has been found according to the invention that in particular foamed silicone rubber, in other words cross-linked silicone, can be produced into a gas exchange membrane with good blood compatibility due to the inert properties of the silicone material. Consequently, the activation of the blood coagulation system is less severe in a gas exchange membrane of foamed silicone than in conventional, unfoamed membranes of PP or PMP. The gas permeability of silicone rubber exceeds the gas exchange performance of polyolefins such as polyethylene (PE) or polypropylene (PP) by more than a factor of 100. With a silicone gas exchange membrane according to the invention, the amount of anticoagulants required is considerably smaller than when using prior-art gas exchange membranes. Other suitable materials for forming the foamed, closed-cell gas exchange membrane are polyethylene (PE), polypropylene (PP) and polyurethane (PU). The foamed material in particular allows a self-supporting design of the gas exchange membrane, with the result that the gas exchange membrane does not require any additional support. The foaming process allows membranes to be produced which have very low wall thicknesses and a high inherent stiffness at the same time. In particular foamed tubes are easier to process than unfoamed tubes because the foamed gas exchange membranes are not prone to collapse. The gas exchange membrane according to the invention can not only be used in an artificial lung but also in other medical applications. An example for this is the use of the gas exchange membrane as a pad for the treatment of burns. In this case, the pad in particular prevents contaminants from entering the burned tissue while allowing a gas exchange to occur which is necessary for wound healing.

Platinum cross-linked foam proved to be particularly suitable for use in a gas exchange membrane. In a gas exchange membrane of foamed, closed-cell silicone rubber, the cold-formed, in particular extruded shape is fixed by cross-linking. Instead of platinum cross-linking, peroxide cross-linking is applicable as well.

A tube-shaped gas exchange membrane allows a particularly compact design of an oxygenator equipped therewith.

This applies in particular to a gas exchange membrane in the shape of a tube bundle.

Tubes with an outer diameter smaller than 1.0 mm, preferably smaller than 0.5 mm, wall thicknesses of the entire foamed tube wall smaller than 0.5 mm, preferably smaller than 0.2 mm, and cavity sizes between 0.01 mm and 0.1 mm, preferably between 0.025mm and 0.075 mm proved to be suitable for providing a high gas permeability as well as a good sealing effect between gas side and blood side of the membrane.

It is another object of the invention to provide a method for the production of a gas exchange membrane according to the invention.

This object is achieved according to the invention by a method for the production of a gas exchange membrane according to the invention, the method comprising the steps of extruding a basic material containing a foaming agent and foaming the extrudate.

A method of this type allows the gas exchange membrane to be produced using mass production processes. The typical cavity size and the distribution of the cavity sizes in the foam are finely adjustable depending on the parameters of the foaming agent together with the extrusion pressure and the nozzle shape. A basic material for silicone elastomers is preferably used. The foaming process usually takes place by the effect of heat in a vulcanizing oven. In the foaming process, the foaming agent releases gases such as $CO_2$ and/or hydrogen.

A tube bundle production where the extrudate is cut into a plurality of tubes of a defined length which are then arranged in a bundle and secured relative to each other is particularly efficient.

A fixation by means of a silicone glue is secure and blood-compatible.

Embodiments of the invention will hereinafter be explained in more detail by means of the drawing in which

BRIEF DESCRIPTION OF THE DRAWING

FIG. 1 is a diagrammatic view of an oxygenator being a component of an artificial lung;

FIG. 2 is an enlarged view of a gas exchange membrane of the oxygenator according to FIG. 1 in the form of a tube of foamed silicone rubber;

FIG. 3 is a diagrammatic view of another embodiment of an oxygenator;

FIG. 4 is an enlarged view of the gas exchange membrane in the oxygenator according to FIG. 3 in the form of a plate of foamed silicone rubber;

FIG. 5 is an enlarged section of FIGS. 2 and 4 of a first embodiment of the foamed silicone; and FIG. 6 is an enlarged section of FIGS. 2 and 4 of a second embodiment of the foamed silicone.

DETAILED DESCRIPTION

An oxygenator 1, which is shown diagrammatically in FIG. 1, serves for the oxygenation of blood in an artificial lung (not shown) of a heart-lung-machine. The general design of an oxygenator of this type is for instance disclosed in EP 0 765 683 B1. The oxygenator 1 is a hollow fiber membrane oxygenator and has a bundle 2 of hollow fibers or microtubes 3 which are accommodated in a housing (not shown) and are secured relative to each other by means of a silicone glue (not shown). According to FIG. 1, oxygen or an oxygen-containing gas enters inner lumina 4 of the tubes 3 from above and exits the inner lumina 4 at the bottom of FIG. 1, as shown by arrows 5. Blood or blood plasma enters gaps 6 between adjacent tubes 3 of the oxygenator 1 from below and exits the gaps 6 of the oxygenator 1 at the top, as shown by arrows 7.

Walls 8 of the tubes 3 act as gas exchange membranes in the oxygenator 1 for transporting oxygen to the blood on the one hand and for removing carbon dioxide produced by metabolic activity from the blood on the other.

Furthermore, these walls 8 allow the transfer of heat from oxygen-containing gas to blood or blood plasma in order to maintain a predetermined temperature thereof.

Each tube 3 has an outer diameter of 0.4 mm. Other outer diameters which are smaller than 1.0 mm are conceivable as well, in particular outer diameters which are smaller than 0.5 mm. The wall thickness of the entire foamed wall 8 of each tube 3 amounts to 0.1 mm. Other wall thicknesses of the entire foamed wall 8 which are smaller than 0.5 mm are conceivable as well, preferably wall thicknesses which are smaller than 0.2 mm.

Each tube 3, and therefore each wall 8, consists of platinum cross-linked or peroxide cross-linked foamed silicone. Cavities 9 in the foam (cf. FIG. 5) have a typical size of between 0.05 and 0.07 mm. Other cavity sizes between 0.01 and 0.1 mm are conceivable as well. Typical cavity sizes between 0.025 and 0.075 mm are preferred; cavity sizes between 0.05 and 0.07 mm are even more preferred. FIG. 6 shows a variant of a foam with a cavity size of approximately 0.015 mm.

The foam of which the wall 8 of the hollow fibers 3 is made is a closed-cell foam, irrespective of the size of the cavities 9. Between the inner lumina 4 and the gaps 6, there is therefore at least one closed microwall or nanowall 10 of silicone. When the cavity 9 has a size according to FIG. 5, there are one to four of such micro/nanowalls 10 between the inner lumen 4 and the gap 6. When the cavity 9 has a size according to FIG. 6, there are six to 50 of such micro/nanowalls 10 between the inner lumen 4 and the gap 6.

The wall thickness of the entire foamed wall 8 exceeds the thickness of the micro/nanowalls 10 between adjacent cavities 9 several times or—in most cases—even multiple times over. The micro/nanowalls 10 have a thickness of for instance in the single-digit range.

The foam of which the tubes 3 are made is a self-supporting foam. It is therefore not necessary for the tubes to be stabilized, for instance by means of additional wall layers.

The tubes 3 in the oxygenator 1 are produced as follows: A silicone basic material, which contains a foaming agent, is at first extruded in the shape of a tube. The extrudate is then passed through a vulcanizing oven where it is foamed. In the foaming process, the foaming agent releases gases in the form of $CO_2$ and hydrogen. The production of toxic gases during the foaming process can be avoided by selecting a corresponding foaming agent. The extrudate is cut into a plurality of tubes 3 with a defined length which are then arranged in bundles 2 and secured relative to each other by means of the silicone glue. Other types of fixation are conceivable as well, for instance by inserting a plurality of loose tubes 3 into a housing where they are held in place.

FIGS. 3 and 4 show another embodiment of an oxygenator 1 comprising an alternative gas exchange membrane in the form of a plate 11. Components and reference values which correspond to those that have already been explained above with reference to FIGS. 1, 2, 5 and 6 have the same reference numerals and are not discussed in detail again.

In the oxygenator 1 according to FIG. 3, oxygen or an oxygen-containing gas flows into a chamber 12 on the right of FIG. 3 from above and exits said chamber 12 at the bottom, as shown by the arrow 5. According to FIG. 3, blood or blood plasma flows into a chamber 13 on the left of FIG. 3 from below and exits said chamber 13 at the top, as shown by the arrow 7. The two adjacent chambers 12, 13 are accommodated in a housing 14 and separated from each other by the plate 11. The plate 11 in turn consists of platinum cross-linked, foamed, closed-cell silicone rubber. The structure and the cavity size of the foam of which the plate 11 is made are identical to those of the foam of the tubes 3 so that the enlarged sections according to FIGS. 5 and 6 therefore apply to the plate 11 as well. The plate 11 has a wall thickness of 0.1 mm. Other wall thicknesses in the range between 0.05 mm and 2.0 mm are conceivable as well, for instance wall thicknesses which are smaller than 1.0 mm, preferably smaller than 0.5 mm, even more preferably smaller than 0.2 mm.

The plate 11 can be produced by extrusion as well, corresponding to the production of the tubes 3 explained above.

The plate 11 is then glued into the housing 14 in such a way as to prevent a direct passage between the chambers 12, 13.

The invention claimed is:

1. A gas exchange membrane (3; 11) for a medical application comprising an arrangement of foamed, closed-cell material, wherein the gas exchange membrane (3; 11) provides a separation of a gas side from a blood side of the gas exchange membrane (3; 11) such that a gas exchange is enabled through the gas exchange membrane (3; 11) and such that unwanted escape of at least one of liquid medium and solid medium is prevented.

2. A gas exchange membrane according to claim 1, wherein said gas exchange membrane (3; 11) is used in an artificial lung.

3. A gas exchange membrane according to claim 1, wherein said gas exchange membrane (3; 11) consists of foamed, closed-cell silicone rubber.

4. A gas exchange membrane according to claim 1, wherein the foamed material is one of platinum cross-linked material and peroxide cross-linked material.

5. A gas exchange membrane according to claim 1, wherein the cavities (9) in the foam have a typical size of between 0.01 mm and 0.1 mm.

6. A gas exchange membrane according to claim 5, wherein the cavities (9) in the foam have a typical size of between 0.025 mm and 0.075 mm.

7. A method for the production of a gas exchange membrane (3; 11) according to claim 1, the method comprising the following steps:
extruding a basic material containing a foaming agent;
foaming the extrudate.

8. A method according to claim 7, wherein a tube-shaped extrudate is produced, with the extrudate being cut into a plurality of tubes (3) of a defined length which are then arranged in a bundle (2) and secured relative to each other.

9. A method according to claim 7, wherein securing takes place by means of a silicone glue.

10. A gas exchange membrane (3; 11) for a medical application comprising an arrangement of foamed, closed-cell material, wherein the gas exchange membrane (3; 11) provides a separation of the gas side from the blood side of the gas exchange membrane (3; 11) such that a gas exchange is enabled through the gas exchange membrane (3; 11) and such that unwanted escape of at least one of liquid medium and solid medium is prevented, wherein the gas exchange membrane (3; 11) is formed in the shape of a bundle (2) of tubes (3).

11. A gas exchange membrane (3; 11) according to claim 10, wherein said tubes (3) are secured relative to each other.

12. A gas exchange membrane according to claim 10, wherein the at least one tube (3) has an outer diameter which is smaller than 1.0 mm.

13. A gas exchange membrane according to claim 12, wherein the at least one tube (3) has an outer diameter which is smaller than 0.5 mm.

14. A gas exchange membrane according to claim 10, wherein the at least one tube (3) has a wall thickness of the entire foamed wall (8) which is smaller than 0.5 mm.

15. A gas exchange membrane according to claim 14, wherein the at least one tube (3) has a wall thickness of the entire foamed wall (8) which is smaller than 0.2 mm.

* * * * *